United States Patent [19]

Shell et al.

[11] Patent Number: 4,616,658
[45] Date of Patent: Oct. 14, 1986

[54] NON-RADIOACTIVELY LABELED MICROSPHERES AND USE OF SAME TO MEASURE BLOOD FLOW

[76] Inventors: William Shell, 435 North Roxbury Dr., Beverly Hills, Calif. 90210; Jackie R. See, 541 Riveria Ct., Fullerton, Calif. 92635

[21] Appl. No.: 706,151

[22] Filed: Feb. 27, 1985

[51] Int. Cl.⁴ ............................................. A61B 5/02
[52] U.S. Cl. ...................................... 128/691; 436/56
[58] Field of Search ............... 128/630, 666, 691, 692, 128/694; 436/56; 424/9

[56] References Cited

FOREIGN PATENT DOCUMENTS 2210406  3/1972  Fed. Rep. of Germany ...... 128/691

OTHER PUBLICATIONS

MacFarland, W. J. et al., "Telemetry of Regional Tissue Blood Flow Using Hydrogen Clearance", Conf: 8th Anm. NE Biongi. Conf., Cambridge, Mass. 27–28 Mar. 1980 (pp. 40–43).
Jacobs, R. et al., "Determination of Acurocies of Dye Dilution and Electromagnetic Flowmeter Methods of Measuring Blood Flow", Jrnl of TCV Surgery v. 58, No. 4, 10/1964.

*Primary Examiner*—Kyle L. Howell
*Assistant Examiner*—Francis J. Jaworski
*Attorney, Agent, or Firm*—Robert J. Schaap

[57] ABSTRACT

A safe and inexpensive method of measuring blood flow in experimental animals using non-radioactively labeled microspheres is provided. The microspheres may be comprised of a variety of materials, including latex and agarose, and may be labeled with colored dyes or by linkage to enzymes, plant enzymes being preferred because they do not occur naturally in an animal's system. After injection and circulation of the microspheres throughout the animal's system, blood flow to particular tissue may be measured by counting the number of microspheres in the tissue sample, the initial number of microspheres in the animal's blood stream having been measured shortly after injection. In the case of microspheres labeled with colored dyes, the spheres may be counted in tissue either after separation from the tissue or while still trapped in the tissue's capillaries. Techniques for separating the microspheres from blood and tissue are also provided.

29 Claims, No Drawings

NON-RADIOACTIVELY LABELED MICROSPHERES AND USE OF SAME TO MEASURE BLOOD FLOW

BACKGROUND OF THE INVENTION

This invention relates generally to the measurement of blood flow and, more particularly, to the measurement of blood flow using non-radioactively labeled microspheres.

The measurement of blood flow in experimental animals is often necessary in the fields of pharmacology, physiology, therapeutics and diagnostics. For example, toxicology studies require blood flow measurement to determine the toxicity of various suspected toxic agents. Further, virtually all diagnostic and therapeutic advances impact on blood flow in some manner. It is therefore desirable to take blood flow measurements.

Blood flow measurements can be performed in many anatomical areas, including the brain, heart, lung, gut, kidney, reproductive organs, skin and muscle. The most sensitive and specific technique used today for measuring blood flow involves the use of radioactively labeled microspheres. In one particular technique, plastic microspheres are marked with a radioactive label and injected into the left atrium of an experimental animal. The spheres disperse in proportion to blood flow. The animal is then sacrificed and the organ of interest is harvested. Blood flow to a particular organ is determined by measuring the level of radioactivity in the organ, which is a function of the number of spheres trapped in the organ's capillaries.

Although the use of radioactively labeled microspheres is sensitive and specific, there are several problems and disadvantages associated with this method. First, startup costs are very high, as they include purchase of a gamma counter to measure radioactivity, lead shielding to protect lab workers from radiation exposure, complex storage facilities and a high minimum "per order" cost of equipment from manufacturers. These high costs severely limit the availability of this type of blood flow measuring apparatus to large labs only.

Second, only five to eight successive measurements per animal can be made using radioactively labeled microspheres, due to the overlap between energies of available radiolabels. Moreover, the measurement of even five blood flow stages requires the use of an extremely complex computer program to analyze and separate the data obtained, further limiting the availability of the technique.

Third, radiolabeled spheres have a limited shelf-life, ranging from one week to several months. Even where the shelf life is at the high end of this range, the continuous decay makes continual recalibration of the testing apparatus necessary.

Fourth, laboratory workers using this apparatus are exposed to substantial radiation danger because many of the isotopes used as labels emit high levels of energy and have long half-lives. In addition, the costs involved in minimizing radiation exposure are substantial.

Finally, disposal of the experimental animals poses significant problems, both logistically and financially. Since the animals remain radioactive for several years after disposal, they must be placed in special low level radiation dumps, to which there is increasing public resistance. The cost of disposal is also becoming prohibitive, recently reaching as high as $500 per animal.

What is needed, therefore, is a method of measuring blood flow that is sensitive and specific, yet is inexpensive to use and does not have the problems associated with a radioactively based method. The present invention satisfies these needs and provides other related advantages.

SUMMARY OF THE INVENTION

The present invention resides in the use of non-radioactively labeled microspheres to measure blood flow, as well as methods of separating them from blood, from body tissue and of determining the number of microspheres in tissue without separation. Measurement of blood flow using the present invention is sensitive and specific, allowing more tests per animal than with radiolabeled spheres. The present method is also relatively inexpensive and poses no health or safety problems for laboratory personnel. Disposal of the experimental animals can be accomplished conventionally, as future radioactive decay is not a consideration.

More specifically, the method of the present invention involves labeling microspheres with colored dyes or enzyme markers. "Labeling" is a commonly used word for marking a substance in such a manner so that the presence of the substance can be later detected. The labeled microspheres are injected into the blood stream of the subject animal via the left atrium. A blood sample is taken shortly thereafter to determine the concentration of microspheres in the animal's bloodstream. As the microspheres are randomly dispersed by blood flow to various tissues in the body, they become trapped in the capillaries of the tissues. The animal is then sacrificed and the tissue of interest is harvested. The microspheres may be separated from the tissue and counted, using a bright line hemocytometer in the case of colored spheres or by measuring optical density to determine enzyme activity in the case of enzyme-linked spheres. Color-dyed microspheres may also be counted while still embedded in tissue. Since the number of microspheres present in tissue is directly proportional to the amount of blood that has flowed through that tissue, the volume of blood flow is statistically calculated from the measurement data and the initial determination of microsphere concentration in the animal's blood.

The microspheres used with the present invention may be of various compositions, including agarose, polystyrene and styrene divinylbenzene, the latter being preferred. The term "microsphere" is used to represent a particle ranging in size from $7\mu$, the size of a red blood cell, to $100\mu$ in diameter. Microspheres within any one size grouping are generally uniform in size. Thus, if a group of microspheres is said to contain particles that are $10\mu$ in diameter, all particles will be roughly $10\mu$ in diameter, with usually no more than a 25% variance.

The microspheres may be labeled in a number of ways, labeling with colored dyes or enzymes being preferred. If colored dyes are used, the dyes should be water insoluble and solvent soluble. An oil-soluble dye will suffice, even if it has some minimal water solubility. If the spheres are to be chemically linked to an enzyme, a variety of enzymes may be used, plant enzymes being most preferred. If an animal enzyme is used, there will be two sources of the enzyme in the final tissue sample: a portion of the enzyme that occurs naturally in the animal's body and the portion that is linked to the microspheres. Therefore, the portion of the enzyme that occurs naturally within the animal's body must be removed from the tissue sample before the activity of the portion of the enzyme that is linked to the microspheres can be measured. If a plant enzyme is used, however, this procedure is not necessary because the only plant enzymes present in an animal tissue sample will be those linked to the microspheres.

Preparation of the microspheres for use consists of first cleaning them, then labeling them as desired. Latex microspheres, for example, are usually stabilized for storage and transport with colloidal silica, such that the microspheres constitute a 10% solids suspension in water. This silica must be removed before labeling the microspheres. After cleaning, the microspheres are labeled either with an oil-based colored dye or with an enzyme, preferably a plant enzyme such as horseradish peroxidase.

The labeled microspheres are injected into the subject animal and allowed time to disperse. Because the labels are so distinct, many tests can be conducted using the same animal. If the microspheres are dyed, there are many easily distinguishable colors that can be used for successive tests within the same animal. If it is desired to link the microspheres with enzymes, a wide variety of enzymes can be used with characteristics such that each can be individually detected.

A blood sample is taken shortly after injection of the microspheres. The microspheres in the sample are separated from the blood and counted to determine the concentration of microspheres per ml of blood. This figure is necessary in computing blood flow to particular tissues, since the number of microspheres that ultimately accumulate in particular tissues will be a function of the initial microsphere concentration in the blood and the volume of blood that flows to the tissue. Because the number of microspheres that accumulate in a particular tissue is randomly determined by the blood flow to that tissue, the amount of blood flow to that tissue can be determined with knowledge of the initial microsphere concentration in the blood and the number of microspheres that become lodged in the tissue. Blood flow is ultimately expressed as a ratio of the number of microspheres that accumulate in tissue (microspheres/gm tissue) to the initial blood microsphere concentration (microspheres/ml blood). This yields blood flow in mls blood/gm tissue, the conventional units for expressing blood flow.

After the desired circulation time has passed, the animal is sacrificed and a tissue sample is taken from the area to which it is desired to measure blood flow. The microspheres can be counted in one of two ways, either after separation from the tissue sample by treatment with collagenase, centrifuging and sedimentation, or without separating them from the tissue sample. The latter method has the advantage of not requiring the separation process, but counting the microspheres while still embedded in tissue capillaries is more difficult than counting after separation.

The procedure for counting the labeled beads depends on the labeling method used. Dyed microspheres are counted after recovery from blood or tissue using a standard ruled hemocytometer, while enzyme-linked microspheres are counted by measuring the optical density of a substrate after reacting the substrate with the enzyme in the recovered sample. The enzyme oxidizes the substrate, and thus the optical density of the oxidized substrate is directly proportional to the amount of enzyme present. Dyed microspheres embedded in tissue are counted using a calibrated microscope.

The blood flow measurement method of the present invention provides dynamic advantages over the radioactive labeling method used in the prior art. Costs are significantly decreased due to the lack of necessity for a radiation counter and protective equipment. The present method is much safer because there is no exposure of lab workers to harmful radioactivity. Disposal of the experimental animals is also facilitated, as they need not be placed in a special radiation dump. This saves money and eases tensions with the public, which often objects strongly to such dump sites.

Other features and advantages of the present invention will become apparent from the following detailed description, which illustrates, by way of example, the principles of the invention.

DETAILED DESCRIPTION OF THE PREFERRED EMBODIMENT

The present invention is embodied in the use of non-radioactively labeled microspheres to measure blood flow, as well as in methods of separating labeled microspheres from tissue and blood and counting the number of microspheres present in a given tissue. More specifically, the method of the present invention involves marking latex, agarose or other types of microspheres with colored dye or enzyme labels. The microspheres are injected into the blood stream of an experimental animal and a determination of the microsphere concentration in the blood is made shortly thereafter. The microspheres are dispersed by bloodflow throughout the body and are trapped in the capillaries of tissues because their diameter is slightly larger than the diameter of the capillaries. The animal is then sacrificed and the tissue of interest harvested. The microspheres may be separated from the tissue and counted, or may be counted without being separated from the tissue. Because the number of microspheres present is a function of the initial blood microsphere concentration, blood flow to particular tissue can be readily calculated as a ratio of the number of microspheres present in tissue over the initial blood microsphere concentration.

The method of the present invention provides significant advantages over the use of radioactively labeled microspheres, which is currently the most common and most specific method used for measuring blood. The present method poses no health hazards to lab workers and costs significantly less to use because there is no need to protect workers from radioactivity, or to purchase radioactivity measurement equipment. Disposal of test animals is also facilitated since they need not be placed in low level radiation dumps, thereby greatly lowering disposal costs and minimizing tension with the public. The present method is also more useful, as more successive blood flow measurements can be obtained from a given test animal.

The term "microsphere" is used to represent particles ranging in size from $7\mu$, the diameter of a red blood cell, to $100\mu$ in diameter. A particular group of "uniformly" sized microspheres may vary in diameter up to around 25%. Thus, a group of $10\mu$ diameter microspheres might range in size from around $8.5\mu$ to around $11.5\mu$ in diameter.

The microspheres of the present invention may be composed of any long chain compound susceptible to cross linking to a solid in which amide or carboxyl groups are exposed or are capable of being exposed by suitable treatment. This includes, but is not limited to, latex materials such as polystyrene and styrene divinylbenzene, agarose, polyalkylcyanoacrylate, albumin, cross-linked albumin, sucrose, starch, cellulose and dextran. The examples set forth herein use styrene divinylbenzene, which is a latex material, and agarose microspheres.

Unlabeled latex microspheres such as those used in the working examples herein are generally stored with a collodial silica coating, the coated spheres forming a 10% solid suspension in water. Before labeling, the microspheres are cleaned by vacuum filtering and drying. Example 1 details the cleaning process.

In order to function in the method of the present invention, the microspheres must be marked in some manner so that their presence in tissue after dispersion by blood flow can be detected. This marking process is commonly known as labeling.

One method of labeling the microspheres is by dying with an oil soluble, water insoluble, colored dye, as shown in Example 2. The spheres are placed in chloroform containing the salt of the particular dye desired. After mixing, the microspheres are filtered, washed and stored for use. If the miscrospheres tend to hold together in clumps, they are disaggregated by grinding. Successful preparations of uniformly dyed microspheres have been made using the following dyes: Oil Red O, Oil Red EGN, Oil Blue N, Sudan I, Sudan II, Sudan Black B and Fat Brown RR.

The microspheres can also be labeled by linking them to an enzyme, the activity of which is measurable after the microspheres have become dispersed within the animal's body. A wide variety of animal, plant and bacterial enzymes may be used as labels. Animal enzymes that may be used include, but are not limited to, $\alpha$-amylase, $\beta$-galactosidase, alkaline phosphatase, glycerol dehydrogenase, lipase and uricase. Plant enzymes include, but are not limited to, horseradish peroxidase, $\beta$-amylase and urease. Bacterial enzymes include, but are not limited to, luciferase and streptokinase.

Plant enzymes are most preferred, as they do not occur naturally in an animal's system. The number of microspheres present in a tissue sample is calculated by measuring the total enzyme activity in the sample. If an enzyme that occurs naturally in an animal's system is used as a label, there will be two sources of that particular enzyme's activity in the tissue sample: the presence of naturally occurring enzyme and the presence of the enzyme that is linked to the microspheres. The portion of naturally occurring enzyme must therefore be removed from the tissue sample before the enzyme activity in the tissue resulting from the presence of the microspheres can be measured. That enzyme's activity in the tissue sample will then be caused only by the presence of enzyme-linked microspheres.

Separation of naturally occurring enzyme may be accomplished by two different methods. The first uses differential centrifugation to completely separate the microspheres, including the linked enzyme, from both particulate and supernatant phases containing naturally occurring enzyme. Several high-speed centrifugations followed by washing with buffer are used until the enzyme activity in successive wash solutions is near zero.

The second method involves impregnating the microspheres with iron prior to injection into the animal's system. After recovery of the microspheres from tissue, they can be separated from particulate and supernatant phases using magnets.

A plant or bacterial enzyme, on the other hand, does not occur naturally in an animal's system. When a tissue sample is taken, enzyme activity can be measured without an additional separation step, since the only plant or bacterial enzyme that will be present in the tissue sample will be the enzyme that was linked to the microspheres. Horseradish peroxidase is the preferred enzyme to be used in conjunction with the present invention.

The linking of horseradish peroxidase to the microspheres, details of which are provided in Example 3, entails first activating the polymer microspheres so that they can react with the enzyme. Activation is accomplished by coupling the microspheres to N-ethoxycarbonyl-2-ethoxy, 1,2-Dihydroquinoline (EEDQ). This forms a mixed carbonic anhydride derivative of the insoluble polymer, which reacts with an amine group of the enzyme in coupling buffer to form a peptide bond. This procedure is dependent on careful pH manipulation, as the stability of EEDQ and the mixed carbonic anhydride vary substantially as a function of pH.

After the microspheres are coupled to the enzyme, they are washed with coupling buffer by sedimenting and resuspending in the buffer. Unused sites on the microspheres are blocked by suspending the spheres in glycine, mixing, vacuum filtering and washing.

Alternatively, agarose microspheres may be labeled by linking with $\beta$-amylase, as shown in Example 4. With this combination, the microspheres do not need to be activated prior to coupling to the enzyme.

The labeled microspheres are injected into the left atrium of the subject animal, as described in Example 8, and permitted to circulate throughout the animal's system. A variety of differently labeled microspheres may be used, as long as they will ultimately be discernible from one another. Unlike radioactively labeled spheres, the number of separate blood flow measurements that can be taken from each animal is limited only by the number of visually discernible colors in the case of dyed microspheres, or by the number of enzymes with chemically distinct properties in the case of enzyme-linked microspheres.

Shortly after injection of microspheres bearing a particular colored dye label into the animal's blood stream, a blood sample is taken as in Example 11. The microspheres are separated from a known volume of blood as shown in Example 5 and are counted using the procedure described in Example 7. If the microspheres are labeled with an enzyme, they can be counted by measuring optical density as shown in Example 10. This procedure yields the initial concentration of microspheres bearing a particular label in the animal's bloodstream, which will be necessary to ultimately determine blood flow to particular tissue. To obtain a measurement of initial microsphere concentration in the bloodstream of a 20 kg dog after injection of five million microspheres, 2.5 to 5 mls of blood must be processed.

Once the microspheres have been dispersed throughout the circulatory system of the subject animal, the animal is sacrificed, after which the tissue to which it is desired to measure blood flow is excised and mapped. In the case of enzyme-linked microspheres embedded in a dog heart, as described in Example 6, biopsy samples are cut, minced and mixed with collagenase. The tissue is digested and centrifuged and the sediment is suspended in Tris-HCl buffer. The enzyme activity in the sample is calculated by reacting the enzyme with an oxdizable substrate. The degree of oxidation of the substrate will change the color of the solution containing the reagents, thereby affecting the optical density. Thus, the enzyme activity, and therefore the number of microspheres present, will be directly proportional to the measured optical density of the oxidized substrate. Once the number of microspheres per gram weight of tissue is determined, a calculation of blood flow as a ratio of microspheres per gram of tissue over the initial concentration of microspheres per ml of blood can be made.

If the microspheres are labeled with colored dyes, they are separated from the tissue, as shown in Example 7, by mixing with collagenase and NaOH, followed by suspension in deoxycholate solution. A Spencer-type bright line hemocytometer is used to count the number of microspheres present, as in Example 8. From the data, the number of microspheres per gram weight of tissue can be calculated for a given color, and blood flow can be determined using the same ratio that is used with enzyme-linked microspheres.

Blood flow measurements from tissue samples using color-dyed microspheres can also be made without separating the microspheres from the tissue, as described in Example 11. Ultra-thin slices of tissue of known thickness, preferably about 10μ, are cut from the tissue sample. The colored microspheres can be visualized directly in the capillaries of the tissue without prior separation. As with the above described methods, microsphere concentration can be calculated per gram of tissue, and thus a direct determination of blood flow can be made from the initial microsphere concentration. Although visualization is more difficult without separation of the microspheres, the lack of necessity of separating the microspheres makes the overall technique extremely easy to use. In addition, measurement in tissue directly allows determination of regional blood flow more precisely than with extraction techniques.

The blood flow measurement method of the present invention is extremely sensitive and versatile. As shown in Example 9, an ischemic area of a dog's heart was clearly detected by using the present method. Example 12 demonstrates the facilitation of multiple successive blood flows using the present invention. By using differently colored microspheres, a reduction of blood flow induced by coronary occlusion was accurately measured, as was the re-establishment of blood flow following reperfusion.

The following examples will serve to illustrate the present invention in accordance with a preferred embodiment.

EXAMPLE 1

Microsphere Cleaning and Preparation for Labeling

The microspheres used with the present invention may be composed of various materials, and are preferably uniform latex particles 11.9μ, ±1.9μ in diameter. These particles may be obtained from Duke Scientific Product No. 7512A, and come as a 10% collcidal silica solid suspension in water.

To prepare the microspheres for labeling, 0.5 ml of the microsphere suspension is vacumm filtered through a Millipore type, 0.45μ pore membrane. Whatman No. 542 filter paper will also suffice. The filter support with the microspheres is oven dired at 50°-70° C. The dry weight of the microspheres recovered is 44-50 mgs.

EXAMPLE 2

Labeling Microspheres with Colored Dye

Microspheres prepared in accordance with Example 1 are added to a dye solution ccnsisting of 15 mgs of dye salt in 1 ml of reagent grade chloroform. The melange, in a screw type tube, is gently mixed end over end at room temperature for 18-24 hours. The melange is transferred to Whatman 1 PS filter paper, which permits the solvent phase to flow through and collects the solids and any contaminating aqueous phase. The dyed microspheres are suspended in situ in 0.025% (w/v) aqueous Triton X 100 solution for transfer to a wash tube. The dyed microspheres can also be scraped off the paper.

The microspheres, suspended in 5 mls of the above Triton X 100 solution, are gently mixed end over end for one hour at room temperature. The microspheres are vacuum filtered as in Example 1 and washed three times in situ with the 0.025% Triton X 100 solution.

If the filtrate at this stage is clear, the preparation is oven-dried at 50°-70° C., as in Example 1. The microspheres slide off the support, after which they are slightly ground with a glass stirring rod and suspended in 2 mls of distilled water. If the filtrate is not clear, the microspheres must be resuspended in 5 mls of the Triton X 100 solution, followed by repetition of the mixing and vacuum filtering steps.

Regardless of whether the filtrate is clear, the microspheres are processed as discussed above. The aqueous phase of the suspension is observed for leaching of color from the dyed microspheres. If this occurs, the aqueous phase is removed and replaced.

Using the above procedures, successful preparations of uniformly dyed microspheres have been prepared using the following dyes: Oil Red O, Oil Red EGN, Oil Blue N, Sudan I, Sudan II, Sudan Black B and Fat Brown RR.

EXAMPLE 3

Coupling of Horseradish Peroxidase to Latex Microspheres

Uniform latex microspheres stabilized with colloidal silica can be obtained from Seragen Diagnostics, Inc., Indianapolis, Ind., and should be cleaned according to the manufacturer's instructions. This involves first shaking the microspheres with 20 wt % NaOH solution, then rinsing thoroughly with deionized water. The microspheres are next shaken with 6N HF solution, and again rinsed throughly with deionized water until the pH of the water after rinsing is the same as the pH of the water before rinsing. Whatman No. 542 filters are used on a Buchner funnel in the above steps to dewater the microspheres, in light of the filters' resistance to both HF and NaOH.

The microspheres are activated with EEDQ according to the procedures disclosed in Sundaram, P.V., *Biochem. and Biophys. Res. Comm.*, 61:2, 667 (1974). After activation, 3000 units of Sigma Type VI horseradish peroxidase (5 mgs/ml) in 0.1 M borate coupling buffer (pH 8.0 containing 0.5 M NaCl) are added to 200 μgs of activated microspheres and mixed end over end at room temperature overnight. The microspheres are sedimented by centrifuging at room temperature for 15 minutes at 2500 RPM. They are then washed three times with coupling buffer by sedimenting and resuspending the buffer. Unused sites on the microspheres are blocked by suspending them in 1M glycine (pH 9) and mixing end over end for two hours at room temperature. The preparation is vacuum filtered and washed sequentially with 0.1M acetate coupling buffer (ph 5.0 containing 0.5M NaCl). The preparation is evaluated by the method disclosed in Porstman et al. *J. Clin. Chem.* 19:435–439 (1981).

EXAMPLE 4

Conjugation of β-Amylase to Agarose Beads

In addition to latex microspheres, it is also possible to use agarose beads, to which the enzyme β-amylase may be easily conjugated. The agarose beads may be obtained as Bio Rad Bio-gel A, 200–400 mesh. The following procedure for coupling the microspheres to β-amylase is modified from Porath, J. And Axen, R., *Methods in Enzymology XLIV,*" Academic Press, N.Y., 1976, page 40.

The gel suspension is first washed to remove the azide preservative. After suspension in distilled water containing 10 mgs/ml sodium meta periodate, the temperature is increased to 45° C. in 20 minutes and is maintained at 45° C. for an additional 100 minutes, during which time the mixture is gently stirred. The oxyagarose product is then vacuum filtered and washed with distilled water.

The oxyagarose prepare above is suspended in 0.4M sodium acetate, pH 6.5. Two mls of the acetate solution is used for each gram of oxyagarose. Five thousand units of β-amylase (Sigma, Type I B) in 0.5 ml of distilled water and 20 μls of cyclohexyl isocyanate are added. The preparation is slowly mixed end over end at room temperature overnight, then vacuum filtered. The coupled agarose-β-amylase is washed sequentially with 0.4M sodium acetate (pH 6.5), 0.01M sodium acetate (pH 4.8 containing 0.5M NaCl), and 0.01M sodium acetate (pH 7.0).

β-amylase activity can be determined by the ability of the preparation to cleave maltose from soluble starch as measured by the dinitro salicylic acid color reaction. This method is discussed in Bergmeyer, U., *Methods of Enzymatic Analysis,* Second English Edition, Academic Press, N.Y., 1974, Vol. 1, page 433.

EXAMPLE 5

Recovery of Microspheres from Blood

The procedure for recovering the microspheres from blood varies, depending on the hematocrit of the blood. For blood samples with a 30% or greater hematocrit, the following procedure is used.

Five mls of heparinized blood are pipetted into 25 mls of hemolyzing solution in a 40 ml conical bottom centrifuge tube. The hyperosmotic hemolyzing solution consists of 85 mls of 0.1% Na₂CO₃ solution and 15 mls of Triton X 100, dissolved by warming. The blood pipettes are rinsed three times with the mixture and the contents of the tubes are mixed by inversion.

After centrifuging at 2500 RPM for 15 minutes at room temperature, the supernates are discarded. The sediments are first washed free of hemoglobin by suspending in 10 mls of distilled water and recentrifuging three times, then suspended in 1 ml of 1N NaOH and heated in a boiling water bath for 10 minutes. After cooling, the digests are transferred with pasteur pipettes to 12 ml graduated centrifuge tubes. These digestion tubes are washed with distilled water three times, the washes being added to the digest and the combined volume being made to 5 mls with distilled water.

After mixing by inversion, the tubes are centrifuged at 2500 RPM for 15 minutes at room temperature. The supernates are aspirated with pasteur pipettes and distilled water is added to each sediment to a final volume of 0.2 ml. Five μls of Tween 80 are added to each mixture and the contents of the tubes are mixed by flicking. Just prior to counting, they are again mixed by filling and emptying a pasteur pipette several times.

For blood samples with less than 30% hematocrit, the ratio of homolyzing solution to blood is reduced. For example, in processing blood with a 20% hematocrit, a one to one ratio of hemolyzing solution to blood is used. The remainder of the procedure is unchanged.

If a blood sample has too voluminous a sediment to digest in 1 ml of 1N NaOH, the volume can be increased to 2 mls, or the concentration can be increased to 2N, or both the volume and the concentration can be increased as indicated. The remainder of the procedure is unchanged.

EXAMPLE 6

Recovery of Enzyme-Linked Microspheres from Tissue by Homogenation

One gram biopsy samples are taken from the desired areas of a tissue. Each of the biopsy samples is minced and digested for 24 hours in 0.05M Tris-HCl buffer (pH 7.4, with 0.1M CaCl₂), 50 mg % of collagenase and 0.1% thimerosal. The tissue is incubated overnight at 37° C. while shaking, and is then homogenized using a hand homogenizer. The solids are washed twice with 0.1M Tris buffer at pH 8, the suspension then being taken up in 2 mls of the same buffer.

Three mls of 2% deoxycholate is added to the above preparation. This suspension is centrifuged and taken up in 0.5 ml of water with thorough mixing. The microspheres are then eluted at 23 mls in graduated cylinders.

EXAMPLE 7

Recovery of Color-Dyed Microspheres from Tissue by Homogenation

Tissue samples from the desired body area weighing approximately 2 grams are finely minced with scissors and transferred to 50 ml Erlenmeyer flasks for digestion in buffered collagenase solution. The buffered collagenase solution is made by dissolving 50 mgs (13,000 units) of collagenase (Sigma Type II c 6885) in 100 mls of 0.05M Tris HCl buffer (pH 7.4, containing 0.015M CaCl₂). One mg/ml thimerosal (ethyl mircuritiol salicylate) is added as a preservative.

Twenty-five mls of buffered collegenase solution are added to each flask and the samples are digested for 16–24 hours at 37° C. either in a stationary water bath or in a shaker bath at 100 RPM. The digested samples are hand homogenized in a 40 ml ten Broeck all glass tissue grinder. The homegenates are transfered to 40 ml conical centrifuge tubes. The tissue grinder is washed 3 times with distilled water, the washes being added to the homegenates and the volume being made to a minimum of 30 mls and a maximum of 40 mls.

After mixing by inversion, the samples are centrifuged at 2500 RPM for 15 minutes at room temperature. The supernates are discarded and the sediments (approximately 2 mls) are taken up in 10 mls of 2N NaOH. A smooth paste is made by adding 1 ml of NaOH drop by drop with mixing after each addition. Four mls of NaOH are then added in small aliquots, followed by 2 ml and 3 ml aliquots, with mixing by glass rod and vortexing after each addition. The preparation must be smooth, creamy and free of lumps.

The NaOH suspensions of the sediments are heated in a boiling water bath for 10 minutes. After cooling, the samples are centrifuged at 2500 RPM for 15 minutes at room temperature, the volumes usually being less than 1 ml. The supernates are discarded and each sediment is suspended in 1 ml of 2% deoxycholate solution in 0.01M Tris-HCl buffer, pH 8.0. These suspensions are transferred to 12 ml graduated centrifuge tubes with pasteur pipettes and the tubes are washed 3 times with the buffered deoxycholate solution. The washings are added to the initial suspensions and the combined volume of each sample is made to 4 mls with the buffered deoxycholate solution.

After mixing by inversion, the samples are centrifuged at 2500 RPM for 15 minutes at room temperature. The supernates are discarded and the sediments (less than 0.5 ml) are made to any convenient volume between 0.2 ml and 0.5 ml with the buffered deoxycholate solution.

EXAMPLE 8

Counting Procedure for Color Dyed Microspheres Recovered from Blood or Tissue Homogenate A Spencer-type bright line hemocytometer is used for counting the color dyed microspheres after recovery from blood, as in Example 5, or tissue, as in Example 7. The screen of the hemocytometer is demarcated by peripheral double and triple lines, taking up a total area of 3 mm×3 mm. This area is further divided into four corner squares, 1 mm×1 mm, each of which is subdivided into 16 smaller squares. The central 1 mm×1 mm square is subdivided into 25 squares, each of which is further subdivided into 16 smaller squares. All of the subdivisions are used as counting aids only.

With the cover glass in place, the sample chamber is 0.1 mm deep. The volume of the chamber delineated by the ruled area is therefore 0.9 mm³ (3 mm×3 mm×0.1 mm).

The sample chamber is filled with solutions resulting from experiments conducted in accordance with Example 5 (recovery from blood) or Example 7 (recovery from tissue). All of the microspheres seen in two of the 0.9 mm³ chambers are counted. It is then possible to calculate the microsphere concentration per cm³ (ml) of blood and per g of tissue. These two figures are then expressed as a ratio to yield blood flow to tissue in ml/g.

EXAMPLE 9

Measurement of Blood Flow in Dog Using Colored Dye Labeled Microspheres

In order to demonstrate the present invention, a mongrel dog weighing 20 Kg was anesthetized and a femoral artery catheter inserted. Upon opening the dog's chest, a left arterial catheter was also inserted. An occlusion of the left anterior descending coronary artery was also performed, the occlusion being designed to provide a normal and an ischemic zone (one in which a reduction of blood flow occurs).

Twenty-five million latex microspheres were cleaned in accordance with Example 1 and color dyed in accordance were Example 2, resulting in their suspension in 0.5 ml of 0.05M phosphate buffer at pH 7.2. The microspheres with thoroughly mixed using a Vortex mixer, mixed with the dog's blood, and injected into the left atrium. A blood sample was taken and the blood was found to contain 1225 microspheres/ml. The dog was sacrificed following the injection and the heart taken, being divided into normal left ventricle, ischemic zone and right ventricle sections.

One gram biopsy samples were taken from the ischemic and normal zones and processed as set forth in Example 7. 0.1 ml of the resulting eluted solution was placed under a white cell counting chamber and counted in accordance with Example 8.

The results of this experiment are summarized in Table I. From this table, it can be clearly seen that the method of this invention was successful in detecting the ischemic zone that was created prior to injection. The left ventricle contained 1,770,000 microspheres/gm (145 mls/100 gm), while the ischemic zone contained only 290,000 microspheres/gm (24 mls/100 gm). A direct calculation of blood flow can be made from a measurement of the number of microspheres present per gram of tissue.

TABLE 1

MEASURING BLOOD FLOW USING MICROSPHERES LABELED WITH COLORED DYE

| Sample # | Microspheres 0.25 ml sediment | Microspheres/ 100 gms tissue | Blood Flow mls/100 gms tissue |
|---|---|---|---|
| Left Ventricle | | | |
| 21 | 791,000 | 1,582,000 | 130 |
| 28 | 824,000 | 1,649,000 | 135 |
| 29 | 270,000 | 1,880,000 | 154 |
| 30 | 493,000 | 1,972,000 | 162 |
| M ± SD | 594,000 ± 262,000 | 1,770,000 ± 185,191 | 145 ± 15 |
| Ischemic | | | |
| 1 | 640,000 | 471,281 | 39 |
| 2 | 381,000 | 333,000 | 27 |
| 3 | 226,000 | 291,000 | 24 |
| 4 | 350,000 | 260,000 | 22 |
| 5 | 330,000 | 246,000 | 20 |
| 6 | 156,000 | 141,000 | 12 |
| M ± SD | 347,167 ± 166,388 | 290,000 ± 109,000 | 24 ± 9 |
| Right Ventricle | | | |
| 11 | 778,000 | 485,000 | 40 |
| 13 | 463,000 | 218,000 | 18 |
| 15 | 521,000 | 793,000 | 65 |
| 17 | 1,036,000 | 656,000 | 54 |
| M ± SD | 699,000 ± 262,000 | 538,000 ± 247,000 | 44 ± 20 |

EXAMPLE 10

Measurement of Blood Flow in Dog Using Microspheres Coupled to Horseradish Peroxidase Microspheres such as those used in Example 9 were coupled to the plant enzyme horseradish peroxidase, as described in Example 3. After biopsy samples of the heart were taken as in Example 9, the procedure of Example 6 was used, up to and including the step of tissue homogenation. The resulting tissue homogenate was taken up in 0.5 ml of 0.1M Tris buffer (pH 8). 0.4 ml of this suspension was overlaid on 5.0 mls of a 20% sucrose solution and cetrifuged for 15 minutes at 2000 rpm. The microspheres were filtered through a 0.22 millipore filter using the same Tris buffer. After washing three times with 0.1M acetate buffer (pH 5), the microspheres were transferred to a vial containing 0.5 ml of the same acetate buffer. This solution was incubated in 0.25 ml of 0-phenylalanine, the reaction being stopped with 0.2 ml of 1M hydrogen sulfate.

The optical density of the resulting solution was measured by reacting the solution with an oxidizable substrate, the results being set forth in Table II. The number of microspheres present is directly proportional to the measured optical density of the substrate from the enzyme reaction. A measurement of blood flow can be calculated from the number of microspheres present, as in Example 9.

TABLE II

MEASURED BLOOD FLOW USING MICROSPHERES LABELED WITH PLANT ENZYME HORSERADISH PEROXIDASE

| SAMPLE # | OPTICAL DENSITY (OD) | OD/gm |
|---|---|---|
| Ischemic | | |
| 3 | 0.142 | 0.573 |
| 5 | 0.089 | 0.191 |
| 6 | 0.204 | 0.576 |
| Left Ventricle | | |
| 25 | 0.308 | 1.548 |
| 26 | 0.290 | 1.450 |
| 27 | 0.432 | 2.170 |

EXAMPLE 11

Counting Procedure for Color Dyed Microspheres Embedded in Tissue Sections

Two and one-half million black dyed microspheres were prepared as in Examples 1 and 2 and injected as in Example 10. Blood was taken after the injection as in Example 12 and an average blood sample was found to contain 1900 microspheres/ml blood.

A $10\mu$ thick section was cut from the heart tissue sample and was examined using a calibrated microscope. The area under the calibrated microscopic field was 265 $mm^2$.

The tissue sample was examined for the presence of black microspheres, the distribution of microspheres within the tissue sample being uneven. Random fields were examined until a total of 20 microspheres were observed. In all, 20 fields were viewed before 20 microspheres were counted, or a total of 5300 $mm^2$ (265 $mm^2 \times 20$ fields). Therefore, the microsphere concentration per unit area was 20 microspheres/5300 $mm^2$, or 1 microsphere/265 $mm^2$. Since the tissue sample was 10 um (0.0010 mm) thick, the microsphere concentration per unit volume was 1 microsphere/(265 $mm^2 \times 0.0010$ mm) = 1 microsphere/0.265 $mm^3$. This translates to 3.77 microspheres/$mm^3$ = 3770 microspheres/$cm^3$. Since one $cm^3$ of tissue weighs 1 gm, this means that there were 3770 microspheres/gm tissue.

From the initial blood measurement, it was known that there were 1900 microspheres/ml blood. Thus, blood flow was 3770 microspheres/gm tissue/1900 microspheres/ml blood = 1.98 ml blood/gm tissue, or 198 mls blood/100 gms tissue.

EXAMPLE 12

Measurement of Blood Flow in Dog Using Multiple Injection of Color Dyed Microspheres to Detect Occlusion and Reperfusion This example was designed to show decreased blood flow to ischemic areas after performing an occlusion and the restoration of blood flow following reperfusion.

Five injections into a 20 kg dog were performed using microspheres prepared following the procedures in Examples 1 and 2. The dog was prepared by the same procedure used in Example 9.

The first two control injections of 2.5 million red microspheres and 2.5 million blue microspheres were performed simultaneously. The third control injection consisted of 2.5 million orange microspheres. Following the three control injections, a 10 minute coronary artery occlusion was performed, after which a fourth injection of 2.5 million black microspheres was made. The occlusion was then released and reperfusion was performed. A fifth injection of 2.5 million white microspheres was performed after stabilization of the reperfusion. After each of the injections, 30 mls of blood was sampled and the number of microspheres per ml and per 30 mls of blood was calculated according to Example 8, the results appearing in Table III.

The dog was sacrificed following the five microsphere injections, and tissue samples were taken and prepared in accordance with Example 7. Blood flow in mls/gm tissue was calculated as in Example 11, from a ratio of known concentration of microspheres in the blood initially (microspheres/ml) to the concentration of microspheres in the final tissue sample (microspheres/gm).

Results of examining tissue samples from five different areas of the heart appear in Table IV. These results show that blood flow was relatively uniform in the base, posterior left ventricle and septum, all non-ischemic areas, ranging from 2.11 to 4.15 mls/gm. Blood flow fell radically during occlusion in the ischemic center and ischemic border areas. Blood flow did not rise in the ischemic center during reperfusion, but did rise in the ischemic border after reperfusion.

This example demonstrates the ease and usefulness of successive injections of differently labeled microspheres to measure blood flow. The reduction of blood flow induced by coronary occlusion was accurately measured, as was the reestablishment of blood flow following reperfusion.

TABLE III

| MICROSPHERES IN INJECTED BLOOD SAMPLES | | |
|---|---|---|
| Color of Microspheres in Blood | Microspheres/ 30 ml blood | Microspheres/ ml blood |
| Blue | 24,720 | 824 |
| Red | 18,000 | 600 |
| Orange | 16,800 | 560 |
| Black | 22,800 | 760 |
| White | 17,200 | 573 |

TABLE IV
MEASURED BLOOD FLOW USING MULTIPLE INJECTIONS OF COLORED DYE LABELED MICROSPHERES

| Sample | Site | Control-Red Microspheres/gm (ml/gm) | Control-Blue Microspheres/gm (ml/gm) | Control-Orange Microspheres/gm (ml/gm) | Occlusion Microspheres/gm (ml/gm) | Reperfusion Microspheres/gm (ml/gm) |
|---|---|---|---|---|---|---|
| 4 | Base | 1340 (2.23) | 1740 (2.11) | 1340 (2.39) | 1740 (2.28) | 1340 (2.33) |
| 22 | Posterior Lt. Ventricle | 1362 (2.27) | 1935 (2.34) | 1670 (2.98) | 2460 (3.23) | 1500 (2.16) |
| 25 | Septum | 1423 (2.37) | 1920 (2.33) | 1350 (2.41) | 3160 (4.15) | 1840 (3.22) |
| 29 | Ischemic Border | 1380 (3.01) | 1650 (2.00) | 1686 (3.00) | 468 (0.62) | 1090 (1.90) |
| 30 | Ischemic Center | 2020 (2.45) | 2180 (3.68) | 1545 (2.75) | 0 (0) | 300 (0.52) |

It should be apparent from the detailed description and working examples provided herein that the present invention provides an accurate, dependable, easy to use, inexpensive and safe method of measuring blood flow in experimental animals. Many of these desirable attributes and advantages stem from the fact that the present invention does not incorporate the use of radioactivity, thereby alleviating the problems associated with prior radioactively base methods.

While various forms of the invention have been disclosed, it will be appreciated that various modifications may be be made without departing from the spirit and scope of the invention. Therefore, the invention is not to be limited, except as by the appended claims.

What is claimed is:

1. A process for measuring blood flow in an animal comprising the steps of:
   (a) non-radioactively labeling microspheres;
   (b) introducing said labeled microspheres into the blood stream of an experimental animal;
   (c) determining the number of microspheres in a known volume of said animal's blood after introduction;
   (d) sacrificing said animal and recovering a portion of said animal's tissue;
   (e) determining the number of microspheres present in a known sample size of said tissue;
   (f) calculating blood flow to said tissue from the results of said determination.

2. A process as set forth in claim 1 wherein said microspheres are counted without separating them from said tissue.

3. A process as set forth in claim 1 wherein said microspheres are separated from said tissue before counting.

4. A process as set forth in claim 3 wherein said microspheres are separated from said tissue using collagenase.

5. A process as set forth in claim 3 wherein said non-radioactive label is a colored dye.

6. A process as set forth in claim 5 wherein said colored dye is oil soluble and water insoluble.

7. A process as set forth in claim 6 wherein said colored dye is selected from the group consisting of Oil Red O, Oil Red EGN, Oil Blue N., Sudan I, Sudan II, Sudan Black B, and Fat Brown RR.

8. A process as set forth in claim 3 wherein said non-radioactive label is an enzyme.

9. A process as set forth in claim 8 wherein the activity of said enzyme is measured using O-Phenylenediamine as a substrate.

10. A process as set forth in claim 8 wherein said enzyme is a plant enzyme.

11. A process as set forth in claim 10 wherein said plant enzyme is horseradish peroxidase.

12. A process as set forth in claim 10 wherein said enzyme is $\beta$-amylase.

13. A process as set forth in claim 1 wherein said tissue is heart tissue.

14. A process as set forth in claim 1 wherein said microspheres are on the order of $7\mu$ to $100\mu$ in diameter.

15. A process as set forth in claim 14 wherein said microspheres are about $10\mu$ in diameter.

16. A process for color dying microspheres comprising the steps of:
   (a) mixing said microspheres with a dye salt and a solvent so that the dye in said dye salt is taken up by said microspheres;
   (b) collecting the dyed microspheres of step (a);
   (c) suspending the dyed microspheres of step (b) in an emulsifier to accomplish disaggregation of the microspheres;
   (d) further disaggregating said dyed microspheres, if necessary; and
   (e) resuspending said dyed microspheres in a storage medium.

17. A process as set forth in claim 16 wherein said emulsifier is Triton X 100 or Tween 80.

18. A process as set forth in claim 16 wherein the further disaggregation of step (d) is accomplished by grinding said dyed microspheres.

19. A process as set forth in claim 16 wherein said storage medium is Triton X 100.

20. A process as set forth in claim 16 wherein said colored dye is oil soluble and water insoluble.

21. A process as set forth in claim 20 wherein said dye salt is the salt of a dye selected from the group consisting of Oil Red O, Oil Red EGN, Oil Blue N, Sudan I, Sudan II, Sudan Black B, and Fat Brown RR.

22. A process for separating microspheres from blood comprising the steps of:
   (a) mixing said blood with an anticoagulating agent to obtain anticoagulation of said blood;
   (b) mixing said blood with a hemolyzing solution to break up the red blood cells in said blood;

(c) removing the hemoglobin from the blood contained in the solution of step (b);
(d) concentrating the microspheres in the solution of step (c); and
(e) dispersing the microspheres in the solution of step (d).

23. A process as set forth in claim 22 wherein said anticoagulating agent is heparin.

24. A process as set forth in claim 22 wherein said blood has a hematocrit of greater than around 30% and the ratio of hemolyzing solution to blood is around 5:1.

25. A process as set forth in claim 22 wherein said blood has a hematocrit of less than around 30% and the ratio of hemolyzing solution to blood is around 1:1.

26. A process for counting color dyed microspheres embedded in a tissue section comprising the steps of:

(a) counting the number of microspheres within a statistically significant area of said tissue section; and
(b) statistically determining the number of microspheres per unit volume of tissue from the counting results in step (a).

27. A process as set forth in claim 26 wherein the number of microspheres per unit volume of tissue is calculated by first determining the total area that must be viewed in order to observe a statistically significant predetermined number of microspheres, then multiplying said area by the thickness of said tissue sample.

28. A process as set forth in claim 27 wherein said statistically significant predetermined number of microspheres is around 20.

29. A process as set forth in claim 26 wherein said tissue section is a heart tissue section.

* * * * *